(12) United States Patent
Fourt et al.

(10) Patent No.: US 9,913,943 B2
(45) Date of Patent: Mar. 13, 2018

(54) TRIGGER ASSEMBLY FOR AN AUTOMATIC INJECTION DEVICE

(71) Applicant: Eli Lilly and Company, Indianapolis, IN (US)

(72) Inventors: Jesse Arnold Fourt, Menlo Park, CA (US); Bradley James Simpson, Oakland, CA (US)

(73) Assignee: Eli Lilly and Company, Indianapolis, IN (US)

( * ) Notice: Subject to any disclaimer, the term of this patent is extended or adjusted under 35 U.S.C. 154(b) by 384 days.

(21) Appl. No.: 14/770,890

(22) PCT Filed: Mar. 7, 2014

(86) PCT No.: PCT/US2014/021496
§ 371 (c)(1),
(2) Date: Aug. 27, 2015

(87) PCT Pub. No.: WO2014/159018
PCT Pub. Date: Oct. 2, 2014

(65) Prior Publication Data
US 2016/0008540 A1    Jan. 14, 2016

Related U.S. Application Data

(60) Provisional application No. 61/782,929, filed on Mar. 14, 2013.

(51) Int. Cl.
*A61M 5/20* (2006.01)
*A61M 5/315* (2006.01)

(52) U.S. Cl.
CPC ........ *A61M 5/2033* (2013.01); *A61M 5/3158* (2013.01); *A61M 5/31501* (2013.01);
(Continued)

(58) Field of Classification Search
CPC ............ A61M 5/2033; A61M 5/31581; A61M 5/3158; A61M 5/31501; A61M 2205/19; A61M 2005/2073
See application file for complete search history.

(56) References Cited

U.S. PATENT DOCUMENTS 2,752,918 A    7/1956 Uytenbogaart
4,561,856 A    12/1985 Cochran
(Continued)

FOREIGN PATENT DOCUMENTS

EP    0470977    2/1992
EP    0653220    5/1995
(Continued)

OTHER PUBLICATIONS

Patent Cooperation Treaty International Search Report and Written Opinion of the International Searching Authority pertaining to International Application No. PCT/US2014/021496. Dated May 20, 2014.

*Primary Examiner* — Kevin C Sirmons
*Assistant Examiner* — Amber Stiles
(74) *Attorney, Agent, or Firm* — M. Daniel Spillman (57) ABSTRACT

A trigger assembly for an automatic injection device which by its operation releases a biased element of the device for movement. The trigger assembly includes a button pressable by a user, and a lock member. Prior to the button being plunged, a blocking element on the button is abutted by a button-engaging surface of the lock member to prevent lock member rotation, thereby allowing an engagement surface on the lock member to remain in engagement with an engagement surface of the biased element so as to restrain motion of the biased element. When the button is plunged, the blocking surface moves clear of the button-engaging surface to allow the lock member to rotate, during which
(Continued)

rotation the engagement surfaces disengage to release the biased element for movement.

6 Claims, 13 Drawing Sheets

(52) U.S. Cl.
CPC . *A61M 5/31581* (2013.01); *A61M 2005/2073* (2013.01); *A61M 2205/19* (2013.01)

(56) References Cited

U.S. PATENT DOCUMENTS

| | | | |
|---|---|---|---|
| 4,744,786 A | 5/1988 | Hooven | |
| 4,877,008 A | 10/1989 | Troubridge | |
| 4,893,805 A | 1/1990 | Eberle | |
| 5,080,649 A | 1/1992 | Vetter | |
| 5,150,933 A | 9/1992 | Myslicki et al. | |
| 5,167,304 A | 12/1992 | Capek | |
| 5,300,030 A | 4/1994 | Crossman et al. | |
| 5,346,480 A | 9/1994 | Hess et al. | |
| 5,393,301 A | 2/1995 | Goldberg | |
| 5,514,097 A | 5/1996 | Knauer | |
| 5,540,664 A | 7/1996 | Wyrick | |
| 5,779,677 A | 7/1998 | Frezza | |
| 6,077,247 A | 6/2000 | Marshall et al. | |
| 6,159,181 A | 12/2000 | Crossman et al. | |
| 6,221,046 B1 | 4/2001 | Burroughs et al. | |
| 6,258,068 B1 | 7/2001 | Kirchhofer et al. | |
| 6,387,078 B1 | 5/2002 | Gillespie, III | |
| 6,454,743 B1 | 9/2002 | Weber | |
| 6,475,194 B2 | 11/2002 | Domici, Jr. et al. | |
| 6,544,234 B1 | 4/2003 | Gabriel | |
| 6,589,210 B1 | 7/2003 | Rolfe | |
| 6,632,198 B2 | 10/2003 | Caizza | |
| 7,066,907 B2 | 6/2006 | Crossman et al. | |
| 7,097,634 B2 | 8/2006 | Gilbert | |
| 7,361,160 B2 | 4/2008 | Hommann et al. | |
| 7,465,289 B2 | 12/2008 | Marshall | |
| 7,563,252 B2 | 7/2009 | Marshall et al. | |
| 7,635,356 B2 | 12/2009 | Stamp | |
| 7,699,816 B2 | 4/2010 | Kirchhofer et al. | |
| 7,758,548 B2 | 7/2010 | Gillespie et al. | |
| 7,901,377 B1 | 3/2011 | Harrison et al. | |
| 8,048,029 B2 | 11/2011 | Gillespie, III et al. | |
| 8,052,653 B2 | 11/2011 | Gratwohl et al. | |
| 8,167,840 B2 | 5/2012 | Matusch | |
| 2003/0105430 A1 | 6/2003 | Lavi et al. | |
| 2004/0024367 A1 | 2/2004 | Gilbert | |
| 2006/0184132 A1 | 8/2006 | Watson | |
| 2006/0258990 A1 | 11/2006 | Weber | |
| 2007/0021720 A1 | 1/2007 | Guillermo | |
| 2007/0173770 A1 | 7/2007 | Stamp | |
| 2009/0012470 A1 | 1/2009 | Barrow-Williams | |
| 2010/0049125 A1 | 2/2010 | James et al. | |
| 2010/0069845 A1 | 3/2010 | Marshall et al. | |
| 2010/0100040 A1 | 4/2010 | Matusch | |
| 2010/0160894 A1 | 6/2010 | Julian et al. | |
| 2011/0034878 A1 | 2/2011 | Radmer et al. | |
| 2012/0022466 A1 | 1/2012 | James et al. | |
| 2012/0197186 A1 | 8/2012 | Matusch | |
| 2013/0060232 A1* | 3/2013 | Adlon ................ A61M 5/2066 604/506 |
| 2013/0123697 A1 | 5/2013 | Ekman et al. | |

FOREIGN PATENT DOCUMENTS

| | | |
|---|---|---|
| EP | 0678303 | 10/1995 |
| EP | 0996473 | 5/2000 |
| ES | 2070782 | 6/1995 |
| GB | 728248 | 4/1955 |
| GB | 2388033 | 11/2003 |
| GB | 2396298 | 6/2004 |
| GB | 2396816 | 7/2004 |
| GB | 2397767 | 8/2004 |
| GB | 2463034 | 3/2010 |
| WO | 9013325 | 11/1990 |
| WO | 9903529 | 1/1999 |
| WO | 00/24441 | 5/2000 |
| WO | 03/092771 | 11/2003 |
| WO | 03/097133 | 11/2003 |
| WO | 04/054645 | 7/2004 |
| WO | 2005/115508 | 12/2005 |
| WO | 2005/115512 | 12/2005 |
| WO | 2005/115514 | 12/2005 |
| WO | 2005/115516 | 12/2005 |
| WO | 2006/106291 | 10/2006 |
| WO | 2006/106295 | 10/2006 |
| WO | 2007/002052 | 1/2007 |
| WO | 2007/002053 | 1/2007 |
| WO | 2007/036676 | 4/2007 |
| WO | 2008/112472 | 9/2008 |
| WO | 2009/092807 | 7/2009 |
| WO | 2011109205 | 9/2011 |
| WO | 20120049468 | 4/2012 |
| WO | 2014062488 | 4/2014 |

* cited by examiner

TRIGGER ASSEMBLY FOR AN AUTOMATIC INJECTION DEVICE

BACKGROUND OF THE INVENTION

The present invention pertains to pharmaceutical injection devices, and, in particular, to a trigger assembly within an automatic injection device.

Patients suffering from a number of different diseases frequently must inject themselves with pharmaceuticals. A variety of devices have been proposed to facilitate these injections. One type of device is an automatic injection device. This type of device typically includes a trigger assembly that when operated by a user causes the device to automatically insert into the user a needle of a syringe that prior to triggering was disposed within the device housing, and then the device automatically injects a dose of medication through that inserted needle.

One shortcoming with some trigger assemblies relates to the large force required to operate them. For example, in some devices the spring force that in essence opposes the trigger operation also is used to directly drive the syringe plunger. With increasing diameter plungers, or in situations where the medication being acted upon by the plunger is more viscous, larger spring forces are required. Trigger assemblies that directly work against the large force springs in a conventional manner therefore may be difficult for some to operate.

Thus, it would be desirable to provide a trigger assembly for an automatic injection device which can overcome one or more of these and other shortcomings of the prior art.

BRIEF SUMMARY OF THE INVENTION

In one form thereof, the present invention provides a trigger assembly for an automatic injection device. The trigger assembly by its operation releases a biased element of the device for movement in a first axial direction relative to a housing of the device. The trigger assembly includes a button pressable by a user, a first engagement surface, a lock member, and a second engagement surface. The button is shiftable in the first axial direction relative to the housing from a first axial position to a second axial position. The button includes a blocking element including a blocking surface and a recessed surface. The recessed surface is spaced in a first angular direction from the blocking surface. The first engagement surface is disposed on the biased element and movable therewith. The lock member is supported within the housing to be rotatable therein and includes a button-engaging element. The second engagement surface is disposed on the lock member for engagement with the first engagement surface. The engagement of the first and second surfaces restrains motion of the biased element in the first axial direction. At least one of the first and second engagement surfaces is ramped for camming effect between the first and second engagement surfaces. The blocking element, when the button is disposed at the first axial position, has the blocking surface in abutting relationship with the button-engaging surface to prevent rotation of the lock member in the first angular direction, which prevention of rotation maintains the second engagement surface in engagement with the first engagement surface. The blocking element, when the button is disposed at the second axial position, has the blocking surface clear of the button-engaging surface to allow the lock member, under influence of the camming effect of the first and second engagement surfaces as the biased element is biased in the first axial direction, to rotate such that the button-engaging element moves in the angular direction toward the recessed surface, the first and second engagement surfaces disengaging as the lock member rotates to release the biased element for movement in the first axial direction.

One advantage of the present invention is that a trigger assembly for an automatic injection device may be provided which allows for a convenient operation by a user by application of a relatively low force on the injection button.

Another advantage of the present invention is that a trigger assembly for an automatic injection device may be provided which is readily tunable during manufacturing design.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 1:
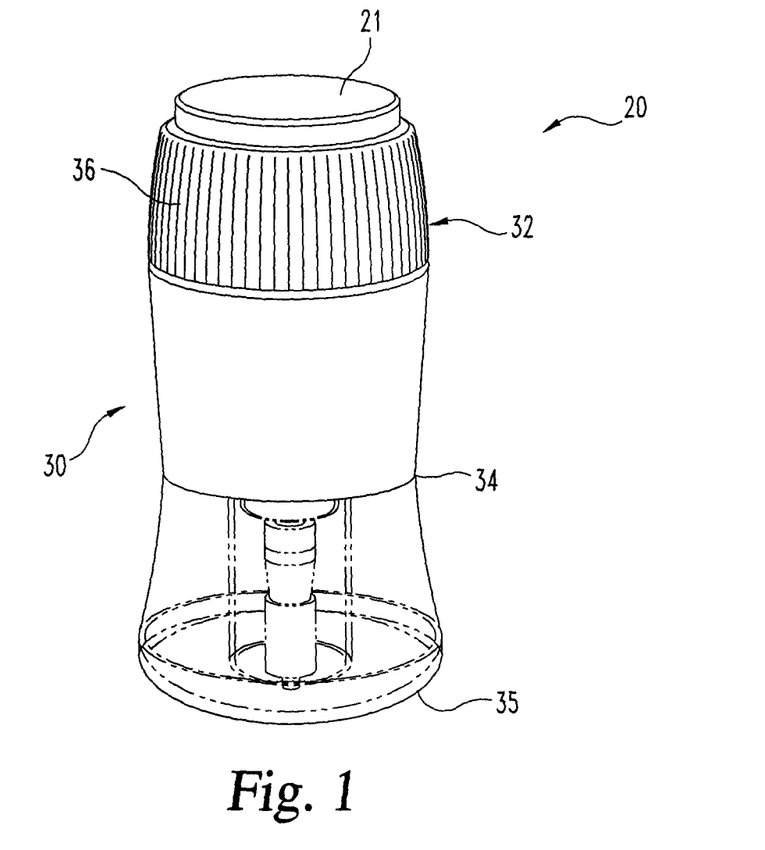
FIG. 1 is a perspective view of an automatic injection device with a trigger assembly of the present invention prior to its use.
Figure 2:
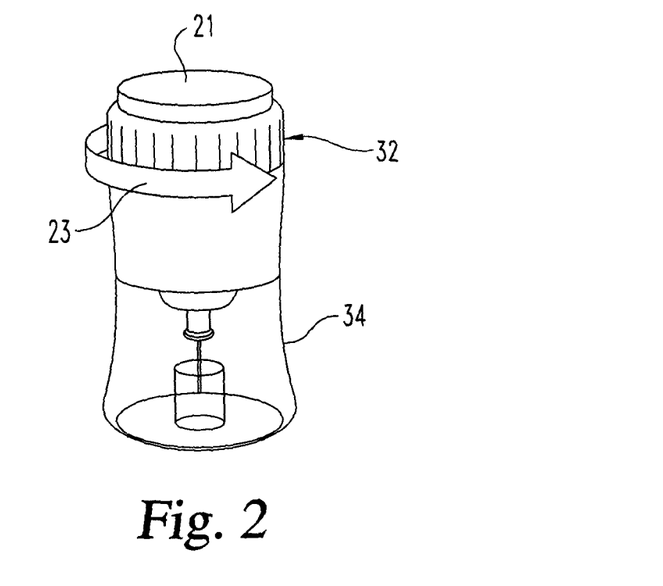
FIG. 2 is an abstract perspective view similar to FIG. 1, but wherein the needle cover is not shown and in which the abstractly shown needled syringe is more readily visible.
Figure 3:
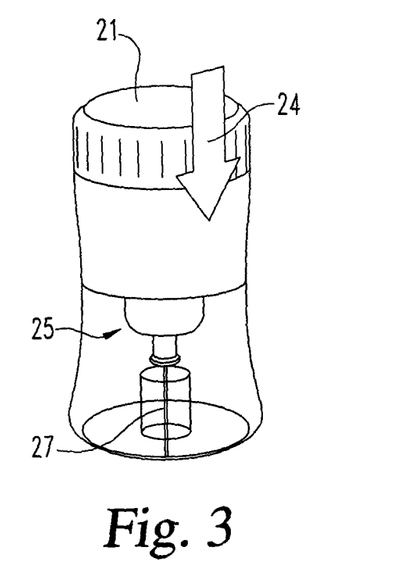
FIG. 3 is an abstract perspective view similar to FIG. 2, but after the device has been triggered, and at a time during use when the needle of the syringe extends from the device for penetrating a user.
Figure 4:
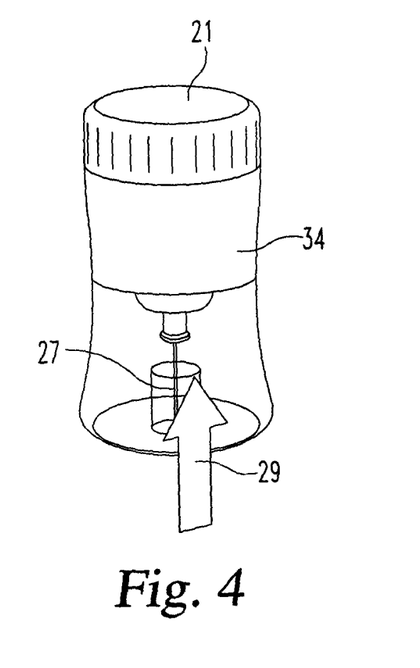
FIG. 4 is an abstract perspective view similar to FIG. 3, but after the device has completed the injection and retracted the needle of the syringe into the housing.

In FIG. 1, there is shown a perspective view of a first embodiment of an automatic injection device, generally designated 20, with a trigger assembly of the present invention. In FIGS. 2-4, device 20 is shown abstractly with a simple needled syringe, and with its needle cover, which during use is collapsed and pierced during an injection, not being shown. FIGS. 1 and 2 show device 20 as it is arranged when in a locked or safety state prior to its use. The device is unlocked by rotating the safety sleeve 32 as indicated by arrow 23 about the housing main body 34 to an unlocked angular position. After device unlocking, and when the inventive trigger assembly is operated by depressing the trigger button, generally designated 21, as indicated by arrow 24, the needled syringe 25 of the device 20 is automatically driven downward such that the injection needle 27 of syringe 25 projects beyond the bottom end of the device housing to penetrate the user as shown in FIG. 3. The device then proceeds to inject automatically, that is without further user action, the medication contents of the syringe 25 through the needle 27, after which the syringe is retracted automatically, as indicated by arrow 29, such that the needle 27 is returned to within the housing as shown in FIG. 4.

Although the inventive trigger assembly is shown finding beneficial application in the device 20 described herein, such application is merely illustrative and not intended to be limiting. The inventive trigger assembly can be used in many different types of automatic injection devices where its benefits are desired, including devices in which the insertion of the needle is manually performed but the forcing of the medicine through the needle is automatic once triggered, as well as devices where the injection refers to the automatic insertion of the needle but the forcing of medicine through the needle is manually powered.

With reference again to FIG. 1, device 20 includes an outer housing 30 in which are operationally disposed working components of the device. The outer housing 30 includes a safety sleeve 32, a main body 34 and a base plate 35 that together form the axial height of the outer housing.

Figure 6A:
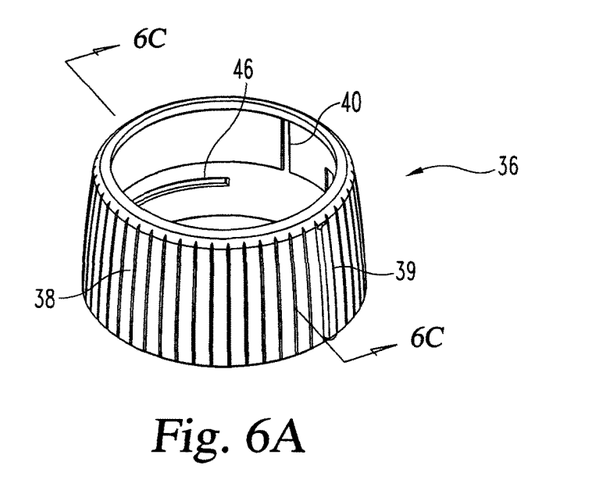
FIGS. 6A, 6B and 6C are respectively perspective, side and cross-sectional views of a housing safety sleeve outer member shown separate from the other components of the device of FIG. 1.
Figure 6B:
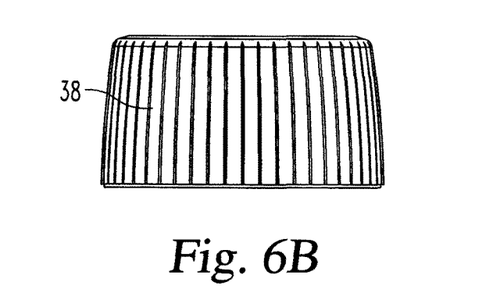
Figure 6C:
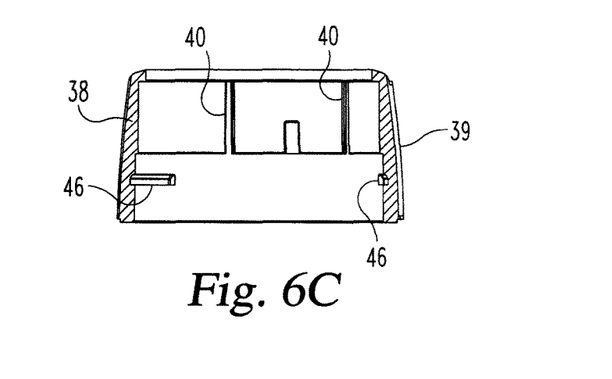
Figure 7A:
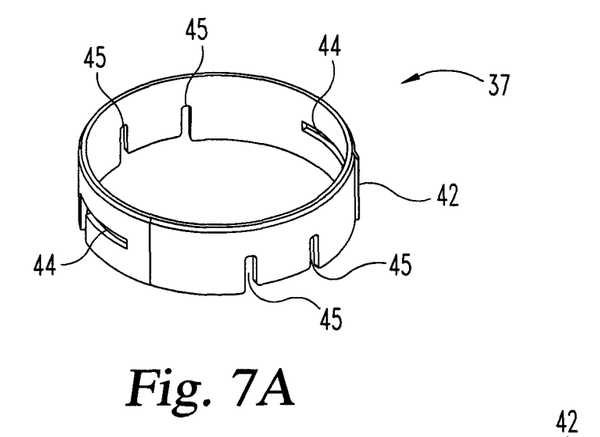
FIGS. 7A, 7B and 7C are respectively perspective, top and side views of a safety sleeve insert shown separate from the other device components.
Figure 7B:
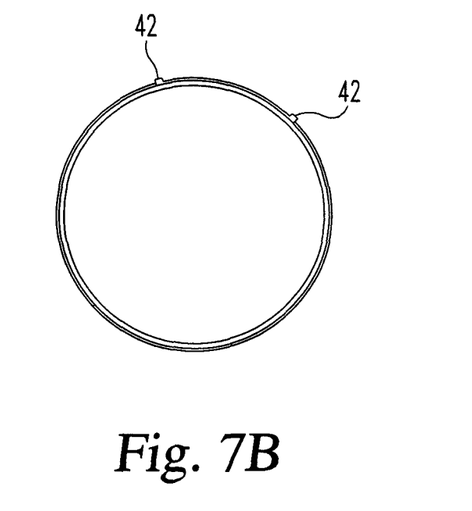
Figure 7C:
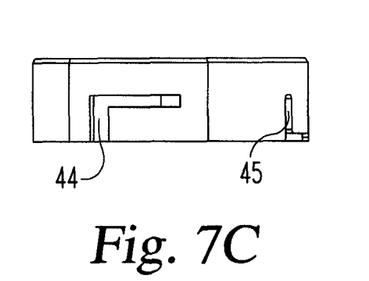

The safety sleeve 32 includes a two-part construction formed of outer sleeve member 36 shown in FIGS. 6A-6C and an insert or inner sleeve member 37 shown in FIGS. 7A-7C. Sleeve member 36 includes a knurled periphery 38 that includes a raised rib 39 that with not shown indicia visible along the housing main body serves to indicate the rotational position of sleeve 32 and thereby the locked or unlocked status of the device. Sleeve member 36 includes axially extending keyways 40 that receive keys 42 of sleeve member 37 to rotatably secure the sleeve members together. Sleeve member 37 is axially retained in one axial direction by a shelf in sleeve member 36 and in the other axial direction by housing main body 34, such that when finally assembly in the device the sleeve members 36 and 37 are fixed axially relative to each other.

A pair of button lock slots 44 are formed in diametrically opposed portions of sleeve member 37. Two pairs of slots 45 extend upward from the bottom of sleeve member 37.

Safety sleeve 32 is mounted to housing main body 34 to be axially fixed and rotatable relative thereto through a small angular distance equal to the angular distance between the slots 45 of each closely spaced slot pair. The insertion of tabs 47 of housing main body 34 within two diametrically opposed channels 46 of sleeve member 36 provides for such mounting.

Figure 9A:
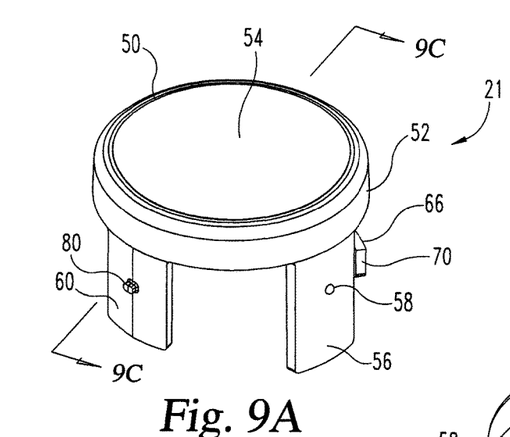
FIGS. 9A, 9B and 9C are respectively top perspective, bottom perspective and cross-sectional views of a button shown separate from the other device components.
Figure 9B:
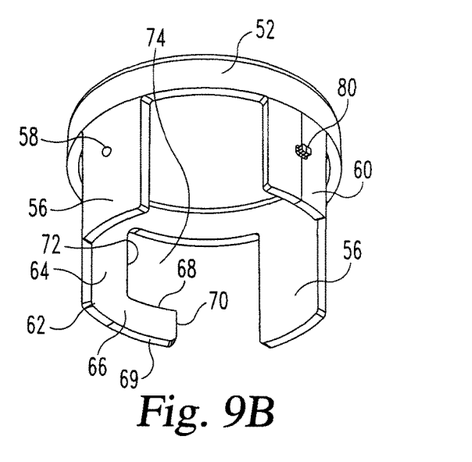
Figure 9C:
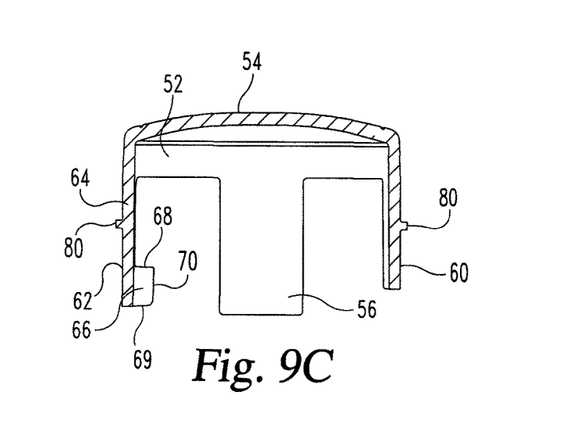

Button 21 is part of the trigger assembly and is shown further in FIGS. 9A-9C. Button 21 is molded as a single piece from a suitably durable material, such as Delrin 570 with 20% glass fill. Button 21 includes an end disc 50 with a skirt 52 extending proximally from the outer periphery of disc 50. End disc 50 has a convex distal face 54 on which a force can be directly applied by a user to selectively plunge the button to trigger the device.

A pair of diametrically opposed resilient arms 56 depend from button skirt 52 and extend in the axial direction. Due to being curved along their angular span, arms 56 are arcuate bar-shaped. Each arm 56 is provided with a detent bump 58 on its radially outward surface. Each bump 58 interacts with one of the pairs of slots 45 formed in sleeve member 37 to provide tactile and audible feedback at the locking and unlocking rotational positions of sleeve 32. Sleeve member 37 may be modified to further include, within the slots 45 in which bumps 58 reside when sleeve 32 is in the unlocking rotational position, not shown features that cooperate with bumps 58 to prevent the button 21 from axially returning to its original, pre-pressed position after it has been fully plunged during use.

A bar-shaped arm 60 of button 21 which curves in the angular direction depends from button skirt 52 between arms 56. Diametrically opposite of arm 60 is an arm 62 that serves as a blocking element in the trigger assembly. Arm 62 includes a first section 64 that is arcuate bar-shaped and that projects axially from skirt 52. Arm 62 also includes a second section 66 which is bar-shaped and projects in the angular direction from, and is arranged orthogonally to, first section 64. Arm section 66 includes a top face 68, a bottom face 69, and an end face 70. End face 70 serves as a blocking surface for a lock member as described further below.

End face 70 is angularly spaced from the side face or surface 72 of arm section 64, resulting in the surface 72 being, in the angular direction, recessed from end face 70. As a result of the configuration of arm 62, a gap or opening 74 is provided in the axial space above arm top face 68 and below skirt 52.

Each of arm 60 and arm first section 64 includes a protruding dog or key 80 on its radially outward surface. Keys 80 fit into button lock slots 44 of sleeve member 37. Until safety sleeve 32 is rotationally oriented on main body 34 such that keys 80 are aligned over the axially extending portions of slots 44, keys 80 cooperate with inner sleeve member 37 to prevent the button 21 from being axially shifted relative to the device housing.

Figure 8A:
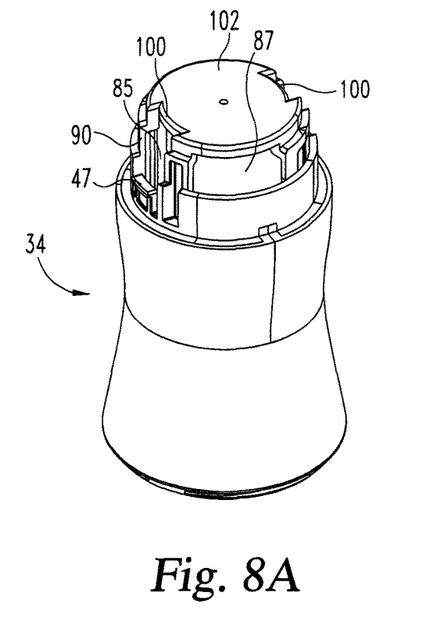
FIGS. 8A, 8B and 8C are respectively perspective, side and top views of a housing main body shown separate from the other device components.
Figure 8B:
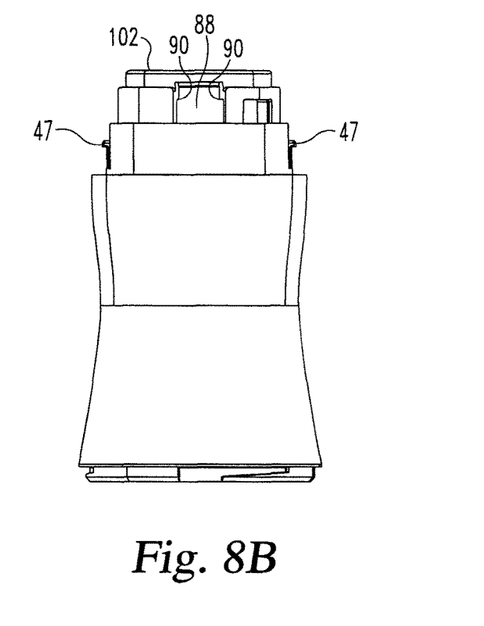
Figure 8C:
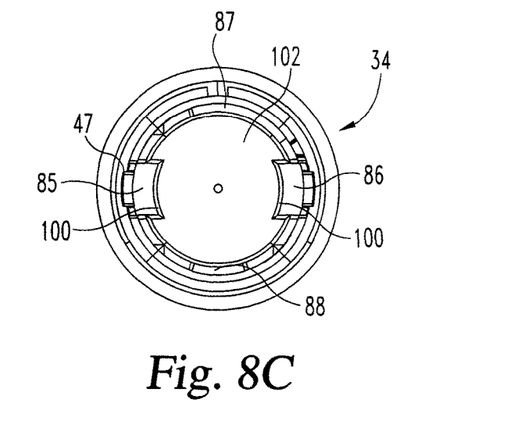
Figure 12:
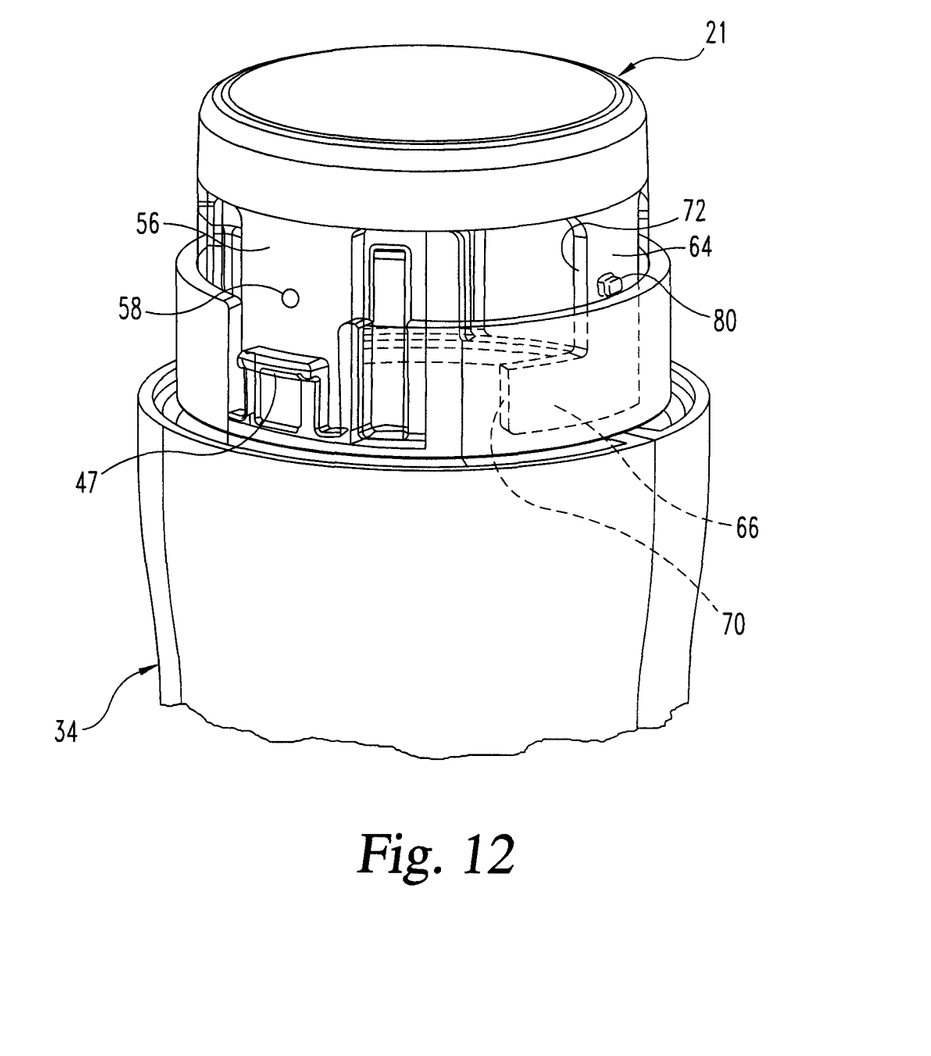
FIGS. 12 is a partial perspective view of only the button assembled to the housing main body, and with the button in a plunged axial position.

As best shown in FIG. 12, button 21 mounts to the upper region of housing main body 34. With additional reference to FIGS. 8A-8C, each of the two arms 56, as well as arms 60 and 62, insert within appropriately sized openings or cut-outs 85, 86, 88 and 87, respectively, provided in body 34 so as to allow button 21 to move axially, but not rotatably, relative to body 34. Guide rails 90 formed along both sides of each of openings 85-87 guide the axial motion of button 21. Reliefs 100 are formed above openings 85 and 86 in the disc-shaped portion 102 of body 34 to allow button arms 56 to flex radially inward to accommodate the detent feature associated with detent bumps 58.

The trigger assembly also includes a movable lock member that cooperates with the blocking element of button 21. The lock member is provided as a ring-shaped member or lock ring 110 shown further in FIGS. 10A-10C. Lock ring 110 is made in one-piece from Delrin 570 with 20% glass fill and includes arc segments 112 and 114 that are spanned by thinner arc sections 116 and 118 which together define a generally circular opening 119. Each arc 112 and 114 includes an angular end 117 that is ramped in the axial direction to provide a ramp or cam face 120. Ramp faces 120 together serve as an engagement surface to engage a complementary member or surface on an element of the drive mechanism of device 20 which is biased in the proximal direction and which is released by operation of the inventive trigger assembly. Cam faces 120 faced distally, which is a direction opposite to the direction the biased element moves when released by the trigger assembly. The manner in which the biased element functions in the drive mechanism of the device is not material to the trigger assembly of the present invention. The description below of the function of that biased member, or plunger element 155, is therefore intended to be illustrative and not limiting.

Figure 10A:
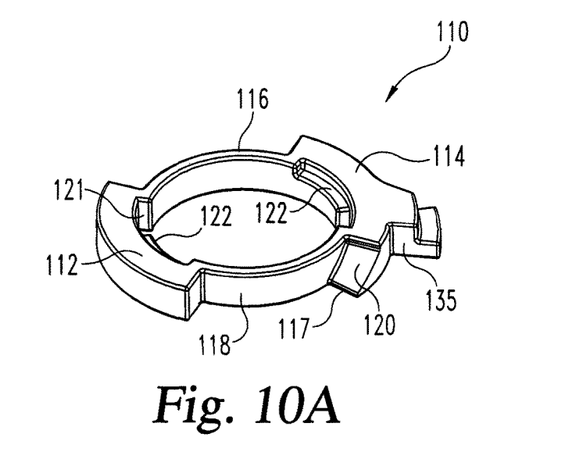
FIGS. 10A, 10B and 10C are respectively perspective, top and side views of a ring-shaped lock member shown separate from the other device components.
Figure 10B:
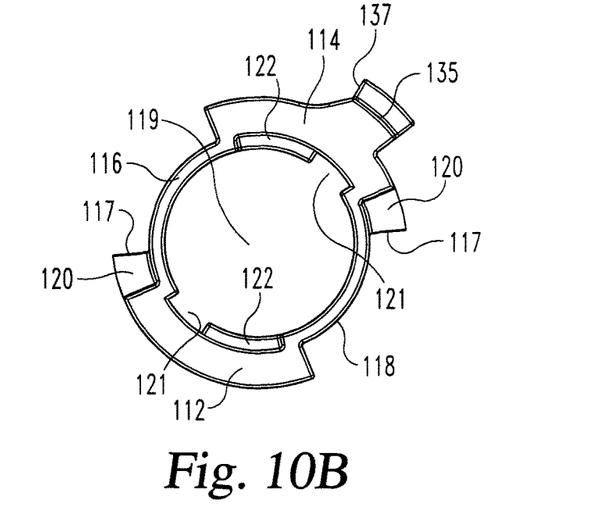
Figure 10C:
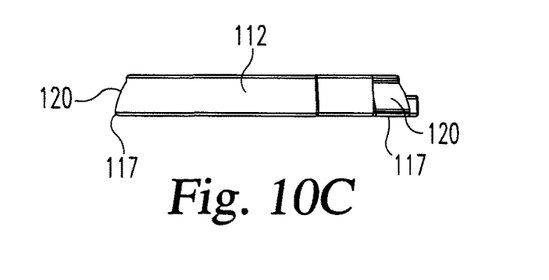
Figure 11A:
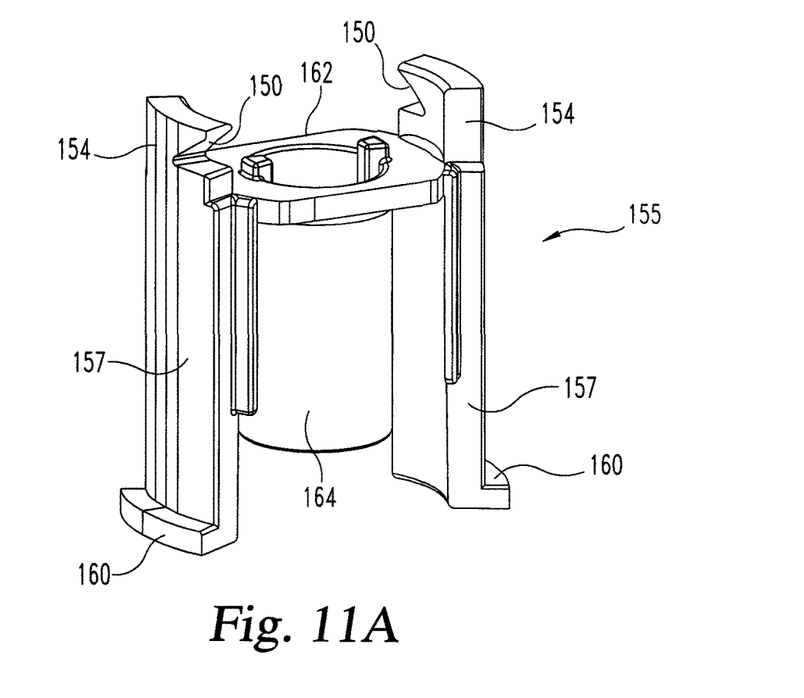
FIGS. 11A, 11B, 11C and 11D are respectively top perspective, bottom perspective front and side views of a plunger element shown separate from the other device components.
Figure 11B:
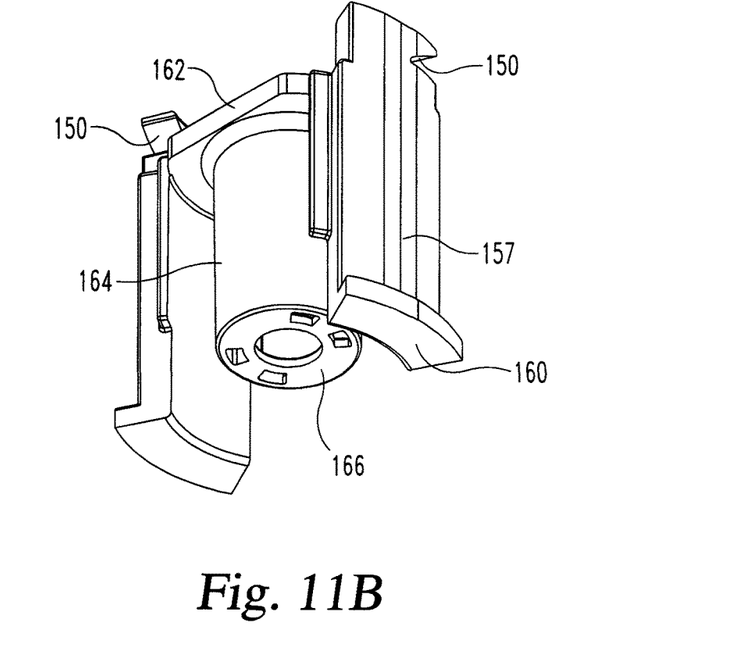
Figure 11C:
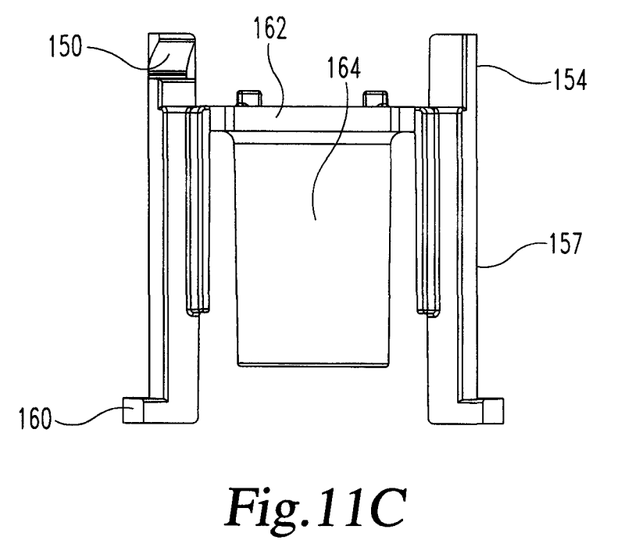
Figure 11D:
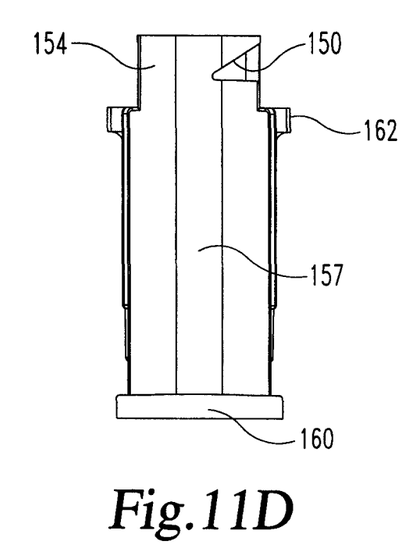

Two ramp faces 120 spaced one hundred eighty degrees apart around the circumference of lock ring 110 serve as the engagement surface to distribute loading on the lock ring 110, but additional angularly spaced faces, such as totaling four spaced ninety degrees apart, could also be used as the engagement surface, or a single ramp face could also be used as the engagement surface.

Figure 5:
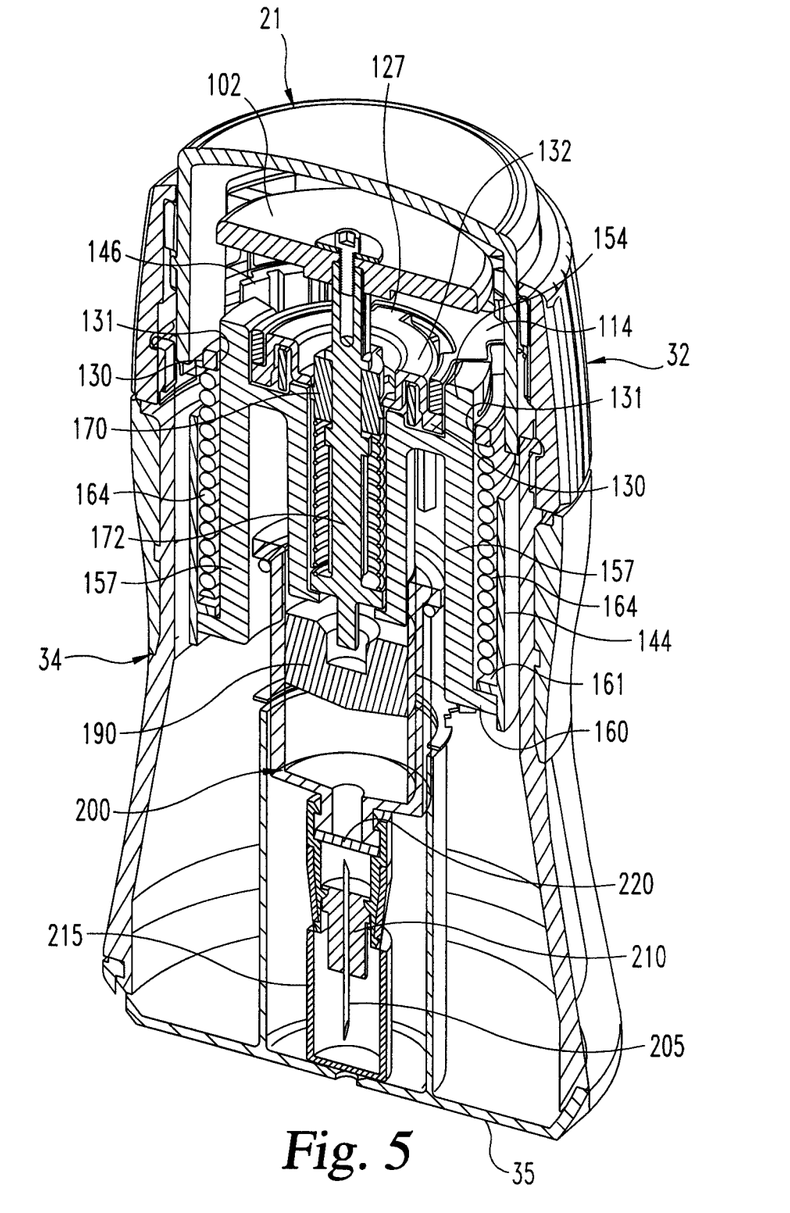
FIG. 5 is a longitudinal cross-sectional view of the automatic injection device of FIG. 1 in which the safety lock of the device is enabled prior to use.

Lock ring 110 is supported within the housing main body 34 such that, during the triggering operation, the lock ring 110 is axially fixed but rotatable within the housing main body 34 around an axis of rotation that extends in the axial direction and in alignment with the center of the housing main body 34. Lock ring 110, in the device 20 as shown in FIG. 5, is so rotatably mounted indirectly to the housing via being rotatably supported on a shuttle member 130 having an upstanding collar 132 which fits within opening 119, with shuttle member 130 being rotationally keyed to plunger element 155, with plunger element 155 being rotationally fixed to a sleeve 144 that is directly rotatably fixed to the housing via keys 146 of that sleeve 144 that fit within axially extending channels defined by not shown internal ribs of housing main body 34. In other applications, the lock ring may be differently supported, such as directly to a shoulder of a housing member, or indirectly to the housing via another component.

Along their inner radial peripheries, each of arc segments 112 and 114 includes a notch 121 and a reduced height shoulder 122. Tabs 127 of shuttle member 130 fit through notches 121 during manufacturing assembly. When assembled, tabs 127 are arranged to protrude above shoulders 122 and freely slide over shoulders 122 during the triggering operation, in so doing locating lock ring 110 axially relative to the shuttle member, which is axially fixed relative to the housing during triggering as further described below.

A step-shaped tab 135 of lock ring 110 projects radially outward from arc segment 114 so as to be located farther from the axis of rotation of lock ring 110 than are cam faces 120. Tab 135 includes an angular side face 137 that extends radially and which serves as a button-engaging surface of lock ring 110. When button 21 is not plunged and arranged as shown in FIG. 1, side face 137 directly abuts arm end face 70 so that lock ring 110 can not rotate toward arm surface 72.

When button 21 is in the plunged position, arm end face 70 is axially below or clear of side face 137, allowing tab 135 to move into opening 74 as the lock ring 110 rotates.

Figure 13:
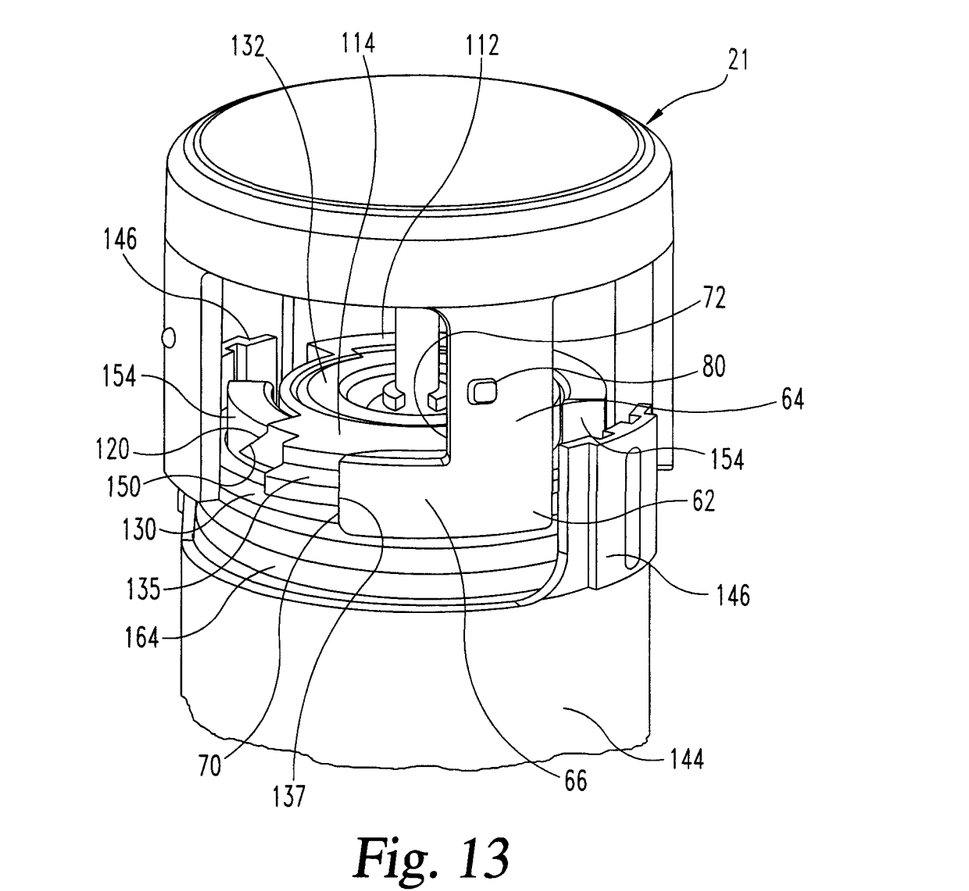
FIG. 13 is a partial perspective view of selected components of the device of FIG. 1 prior to operation of the trigger assembly.

As shown in FIG. 13, prior to device triggering, the lock ring cam faces 120 engage two complementary cam faces 150 provided on upper regions 154 of a plunger element, generally designated 155. Cam faces 150 are faced downward, which is the direction the biased plunger element 155 moves when released by the trigger assembly as described below. Cam faces 150 together serve as the engagement surface of plunger element 155 that engages the lock ring 110. Upper regions 154 extend through openings 131 provided in the shuttle member 130 to which plunger element 155 is keyed to be axially movable but rotatably fixed. In a not shown alternate embodiment, the plunger element upper regions, and the openings in the shuttle member through which the upper regions extend, may be reduced in outside diameter without change to the lock ring 110, which results in the shuttle being able to provide stress-reducing support for the outer radial periphery of lock ring ends 117. In alternate embodiments having different numbers of lock ring cam faces 120, the plunger element cam faces 150 are preferably in a one to one and positional correspondence with such cam faces 120.

In the shown embodiment, faces 120 and 150 are each ramped. The angle of the ramping of faces 120 and 150 is approximately fifty degrees relative to the axial direction. During development of the device, different angles can be provided for the mating faces 120, 150 to tune the trigger assembly feel as different angles result in different frictional forces that affect the force needed to plunge button 21 to trigger the device. In alternate embodiments, different camming features may be provided. For example, camming can be achieved with only one of each pair of engaging faces 120, 150 being ramped.

Plunger element 155 is further shown in FIGS. 11A-11D and includes upstanding legs 157 with flanged ends 160. The flange ends 160 are effectively acted on by the bottom end of a coil spring 164 through a shoulder 161 of sleeve 144, which shoulder is disposed between flange ends 160 and spring 164. The top end of spring 164 acts against the underside of a plate shape portion of shuttle member 130. When plunger element 155 is engaged with lock ring 110 via the engagement of cam faces 120 and 150 as shown in FIG. 5 and FIG. 13, spring 164 is captured in a compressed state between the shuttle member 130 and the plunger element 155, causing plunger element 155 to be biased downward relative to the shuttle, which during triggering is axially held in place in the housing by its engagement with a follower 170 supported by an axially extending housing support member 172 fixed to housing portion 102, as can be further understood in view of a provisional patent application filed with the United States Patent and Trademark Office on Mar. 14, 2013 as Application No. 61/783007, and in view of an international patent application, with the same listed inventors as this case, filed with the United States Patent and Trademark Office as receiving office on the same date of this application and entitled "Delay Mechanism Suitable For Compact Automatic Injection Device", the entire disclosures of both those applications being hereby incorporated herein by reference.

A central plate portion 162 of plunger element spans its legs 157. A cylindrical tube 164 with a partially closed bottom end 166 depends from plate portion 162 between plunger legs 157. Bottom end 166 is for directly engaging a sealing piston or plunger 190 of the device syringe subassembly 200. The downward or proximal driving of piston 190 by plunger element 155 first causes the proximal tip of the needle 205 held within a detented carrier 210 to be driven through the closed proximal end of a collapsing needle cover 215 and through the housing opening into the user, and then causes the contents of the syringe to be expelled from the device 20 through the needle 205 after the distal tip of needle pierces the septum 220. The syringe subassembly does not form a part of the inventive trigger assembly, but will be further understood in view of a conceptually similar subassembly described in International application no. PCT/US2012/051702, the entire disclosure of which application is hereby incorporated herein by reference.

The device 20 could use different types of syringes, such as a staked needle syringe similar to what is shown in FIGS. 2-4. Such a staked needled syringe may have a different sealing cover instead of the collapsing cover shown. For example, it could have a sealing cover that is manually removed by a user prior to use, such as by a finger pullable collar that grips the sealing cover, or by a hand graspable flexible strap, possibly marked with device operating instructions, that hangs from a collar that grips the sealing cover.

The construction of the inventive triggering assembly will be further understood in view of a description of the initial operation of device 20. Device 20 is configured in a locked state as shown in FIG. 5, with the triggering assembly configured as shown in FIG. 13. If a user applies a plunging force on button 21, button travel is frustrated by keys 80 axially abutting inner sleeve member 37.

After a user manuals rotates safety sleeve 32 to the unlocked position and then arranges device 20 on an injection site, button 21 can by plunged by a user. Prior to this button plunging, the triggering assembly is still configured as shown in FIG. 13. In such configuration, the tendency of lock ring 110 to rotate away from plunger element 155, such tendency resulting from the engagement of the cam faces 120 with cam faces 150 and the downward biasing force applied by spring 164 on the rotatably fixed plunger element 155, is prevented by the abutting engagement of end face 70 by lock ring side face 137.

Figure 14:
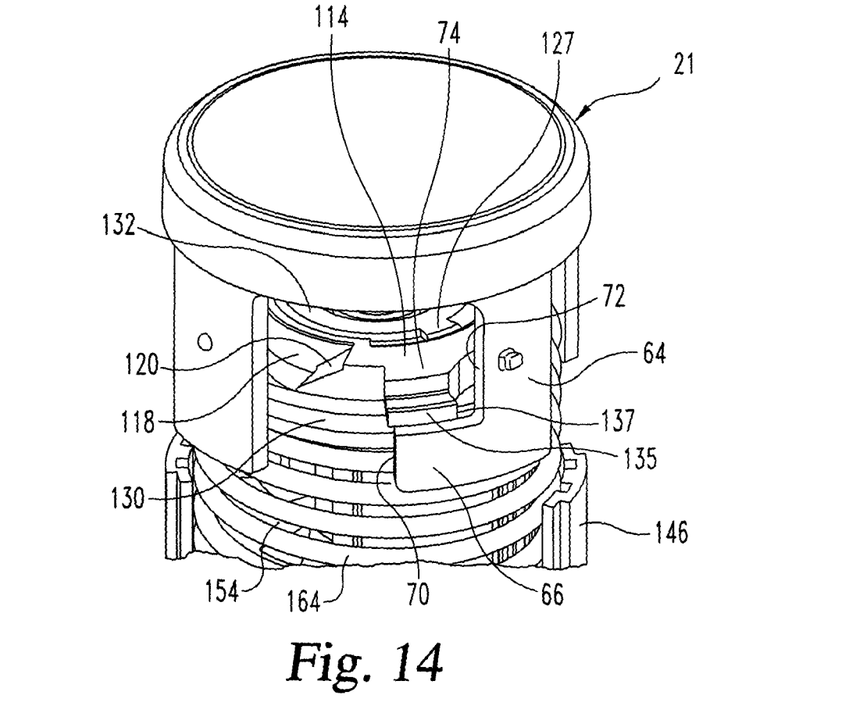
FIG. 14 is a partial perspective similar to FIG. 13 after the trigger assembly has been operated and the plunger element, released by operation of the trigger assembly, has been biased to move axially downward for further operation of the device.

When a user manually applies a plunging force to button distal face 54, button 21 is pushed further into safety sleeve 32 and toward housing main body 34. The force needed to be applied by the user during this plunging process is largely to overcome a frictional sliding force between end face 70 and lock ring side face 137. Additional detenting features between the button and surrounding parts may also be useful to attenuate the button feel, and to hold the button down after triggering such as described above. When button 21 is fully plunged, at which point the keys 80 abut a shoulder on housing main body 34, button arm 62 has shifted axially such that end face 70 no longer is abutted by lock ring side face 137 as arm section 66 is shifted downward within the housing to be axially clear of tab 135. Lock ring 110 is therefore free to rotate, resulting in lock ring side face 137 traveling toward arm surface 72 due to the camming effect of cam faces 120 with cam faces 150 and the downward spring biasing of plunger element 155. When lock ring 110 has rotated to a point where cam faces 150 are angularly clear of cam faces 120, the triggering is complete and spring 164 forcibly moves plunger element 155 downward as shown in FIG. 14 to continue device operation. The device 20 then proceeds to insert the needle 205 into the user, inject the drug product held within the syringe, and then ultimately retract the needle within the housing in accordance with its designed for operation.

While this invention has been shown and described as having preferred designs, the present invention may be modified within the spirit and scope of this disclosure. For example, while the biased element that the trigger assembly releases in the shown embodiment is the plunger element that itself contacts the syringe piston, the inventive trigger assembly could be used to release different biased elements in alternate embodiments, or elements that are biased with parts different than coiled springs. Furthermore, the inventive trigger assembly can be used in devices having different operational principles or parts. This application is therefore intended to cover any variations, uses or adaptations of the invention using its general principles. Further, this application is intended to cover such departures from the present disclosure as come within known or customary practice in the art to which this invention pertains.

We claim:

1. A trigger assembly for an automatic injection device including a biased element and a housing, the biased element releaseable by operation of the trigger assembly for movement in a first axial direction relative to the housing, the trigger assembly comprising:

a button pressable by a user, said button shiftable in the first axial direction relative to the housing from a first axial position to a second axial position, said button including a blocking element including a blocking surface and a recessed surface, said recessed surface being spaced in a first angular direction from said blocking surface;

a first engagement surface disposed on the biased element and movable therewith;

a lock member supported within said housing to be rotatable therein, said lock member including a button-engaging element;

a second engagement surface disposed on said lock member for engagement with said first engagement surface, said engagement of said first and second engagement surfaces restraining motion of the biased element in the first axial direction;

at least one of said first and second engagement surfaces being ramped for a camming effect between said first and second engagement surfaces;

said blocking element, when said button is disposed at said first axial position, having said blocking surface in abutting relationship with said button-engaging element to prevent rotation of said lock member in said first angular direction, which prevention of rotation maintains said second engagement surface in engagement with said first engagement surface; and said blocking element, when said button is disposed at said second axial position, having said blocking surface clear of said button-engaging element to allow said lock member, under influence of the camming effect of said first and second engagement surfaces as the biased element is biased in the first axial direction, to rotate such that said button-engaging element moves in the angular direction toward said recessed surface, said first and second engagement surfaces disengaging as said lock member rotates to release the biased element for movement in the first axial direction.

2. The trigger assembly of claim 1 wherein said lock member comprises a ring having an axis of rotation that extends in said first axial direction and is centered within said housing.

3. The trigger assembly of claim 2 wherein said second engagement surface comprises first and second portions that extend angularly and are spaced 180 degrees apart around said ring for engagement with corresponding portions of said first engagement surface.

4. The trigger assembly of claim 2 wherein each of said first and second engagement surfaces are ramped for camming effect.

5. The trigger assembly of claim 1 wherein said lock member comprises a ring having an axis of rotation that extends in said first axial direction, wherein relative to said axis of rotation said button-engaging element is disposed radially outward of said second engagement surface.

6. The trigger assembly of claim 1 wherein said button comprises an end disc, wherein said blocking element of said button comprises an arm disposed at the periphery of said end disc, said arm including a first section and a second section, said first section projecting axially and including a side face that defines said recessed surface, said second section projecting in the angular direction from said first section and including an end face that defines said blocking surface.

* * * * *